United States Patent
Enge

(10) Patent No.: US 11,141,538 B2
(45) Date of Patent: Oct. 12, 2021

(54) MEDICAMENT DELIVERY DEVICE

(71) Applicant: SHL MEDICAL AG, Zug (CH)

(72) Inventor: Kasper Enge, Järfälla (SE)

(73) Assignee: SHL MEDICAL AG, Zug (CH)

( * ) Notice: Subject to any disclaimer, the term of this patent is extended or adjusted under 35 U.S.C. 154(b) by 306 days.

(21) Appl. No.: 16/348,849

(22) PCT Filed: Dec. 27, 2017

(86) PCT No.: PCT/EP2017/084605
§ 371 (c)(1),
(2) Date: May 9, 2019

(87) PCT Pub. No.: WO2018/130415
PCT Pub. Date: Jul. 19, 2018

(65) Prior Publication Data
US 2020/0188600 A1  Jun. 18, 2020

(30) Foreign Application Priority Data

Jan. 13, 2017 (EP) .................................. 17151421

(51) Int. Cl.
*A61M 5/315* (2006.01)
*A61M 5/31* (2006.01)

(52) U.S. Cl.
CPC .... *A61M 5/31553* (2013.01); *A61M 5/31511* (2013.01); *A61M 5/31541* (2013.01);
(Continued)

(58) Field of Classification Search
CPC .......... A61M 5/31553; A61M 5/31513; A61M 5/31541; A61M 5/31543; A61M 5/31576;
(Continued)

(56) References Cited

U.S. PATENT DOCUMENTS 5,226,896 A  7/1993  Harris
6,086,559 A *  7/2000  Enk ........................ A61M 5/482
                                                          604/121
(Continued)

FOREIGN PATENT DOCUMENTS

CN  102137692 A  7/2011
EP    3064239 A1  9/2016
(Continued)

OTHER PUBLICATIONS

Chinese Office Action for CN Application No. 201780076278.9, dated Feb. 20, 2021.
(Continued)

*Primary Examiner* — Nathan R Price
*Assistant Examiner* — Tasnim Mehjabin Ahmed
(74) *Attorney, Agent, or Firm* — McDonnell Boehnen Hulbert & Berghoff LLP

(57) ABSTRACT

A medicament delivery device (IO) is presented having a housing and a medicament container holder arranged movable in relation to the housing and capable of accommodating a medicament container. The device also has an activator having a plunger rod arranged to be moved in the proximal direction of the medicament delivery device by the activator to act on a stopper in the medicament container for delivering a dose of medicament through a medicament delivery member when the activator is operated. A delay mechanism is also arranged between the activator and the plunger rod, which is provided with delay elements allowing movement of the activator in the proximal direction after movement of the plunger rod has terminated.

20 Claims, 15 Drawing Sheets

(52) U.S. Cl.
CPC .... *A61M 5/31543* (2013.01); *A61M 5/31576* (2013.01); *A61M 2005/3126* (2013.01); *A61M 2005/3143* (2013.01); *A61M 2205/581* (2013.01); *A61M 2205/582* (2013.01)

(58) Field of Classification Search
CPC ............ A61M 5/31561; A61M 5/3158; A61M 5/31593; A61M 5/24; A61M 2205/581; A61M 2205/582; A61M 2205/583
See application file for complete search history.

(56) References Cited

U.S. PATENT DOCUMENTS

| | | | | |
|---|---|---|---|---|
| 2005/0222540 | A1* | 10/2005 | Kirchhofer | A61M 5/31553 604/207 |
| 2013/0211330 | A1* | 8/2013 | Pedersen | A61M 5/2033 604/111 |
| 2015/0133869 | A1 | 5/2015 | Streit et al. | |
| 2017/0182253 | A1* | 6/2017 | Folk | F16F 9/361 |

FOREIGN PATENT DOCUMENTS

| | | |
|---|---|---|
| JP | 2010-535555 A | 11/2010 |
| WO | 2010023303 A1 | 3/2010 |
| WO | 2015/185311 A1 | 12/2015 |
| WO | 2016/193622 A1 | 12/2016 |

OTHER PUBLICATIONS

European Office Action for EP App. No. 17828926.0 dated Jul. 21, 2020.

International Search Report and Written Opinion for Int. App. No. PCT/EP2017/084605, dated Mar. 26, 2018.

* cited by examiner

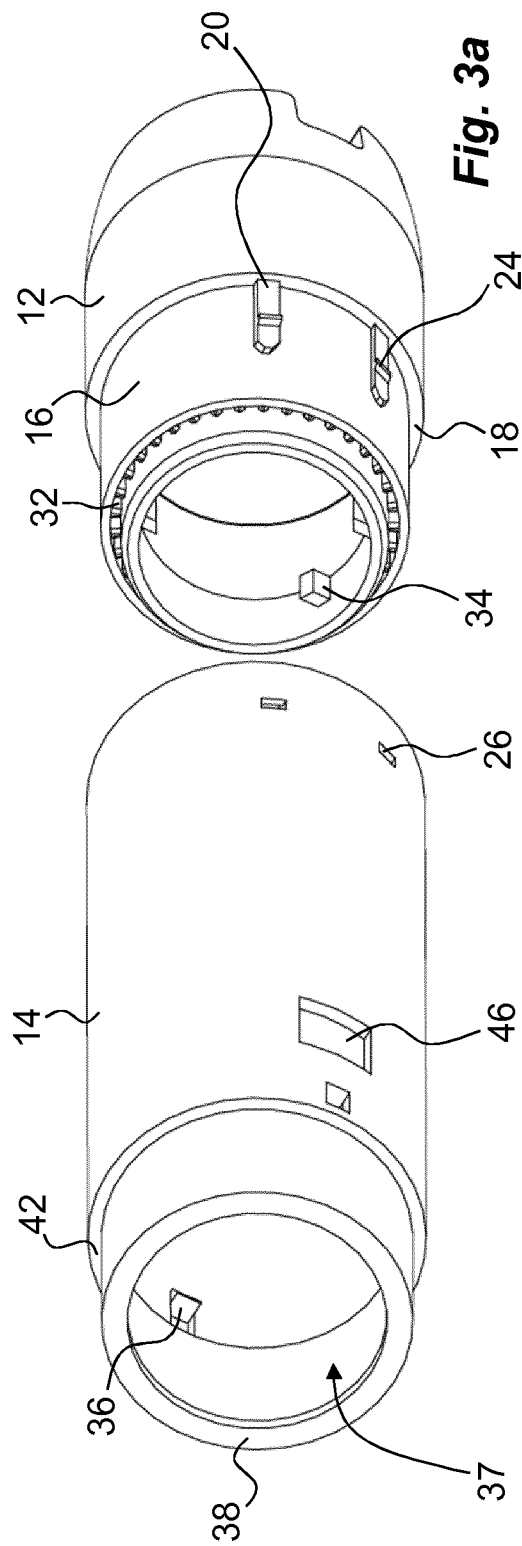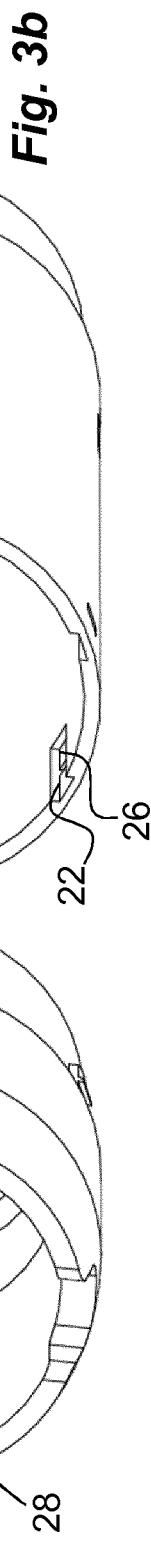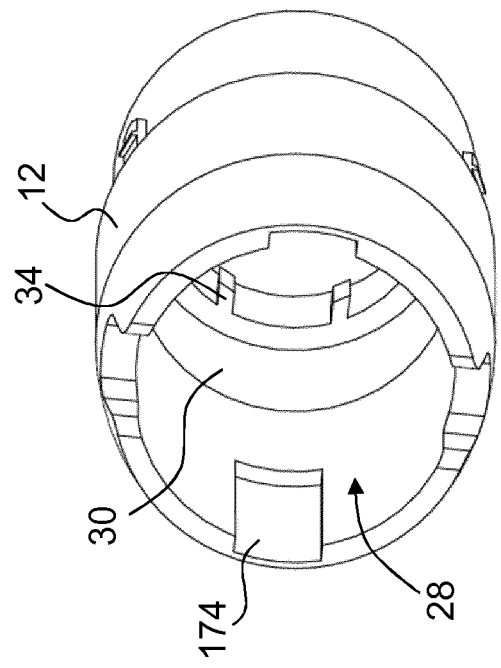
Fig. 3a
Fig. 3b

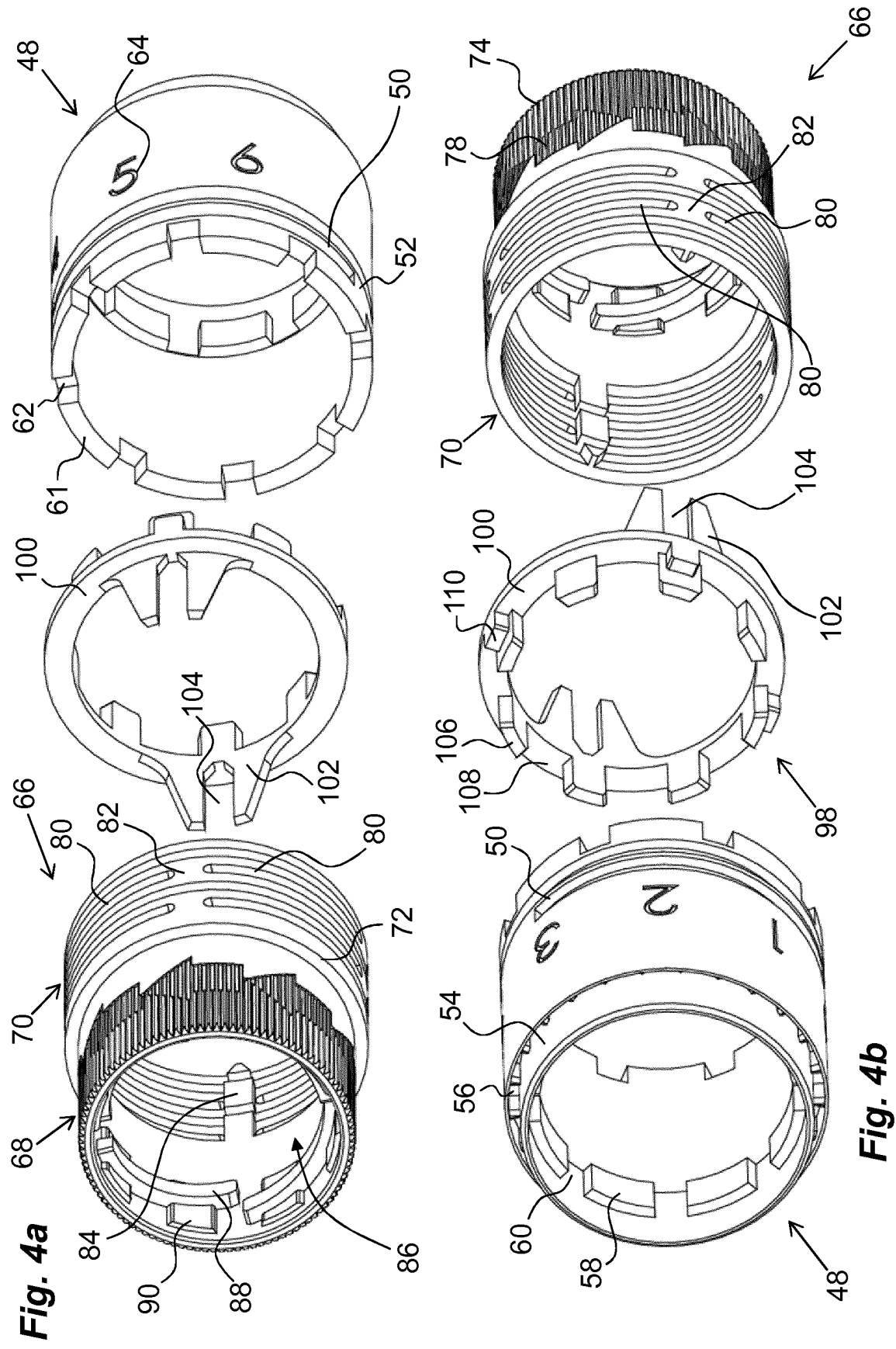

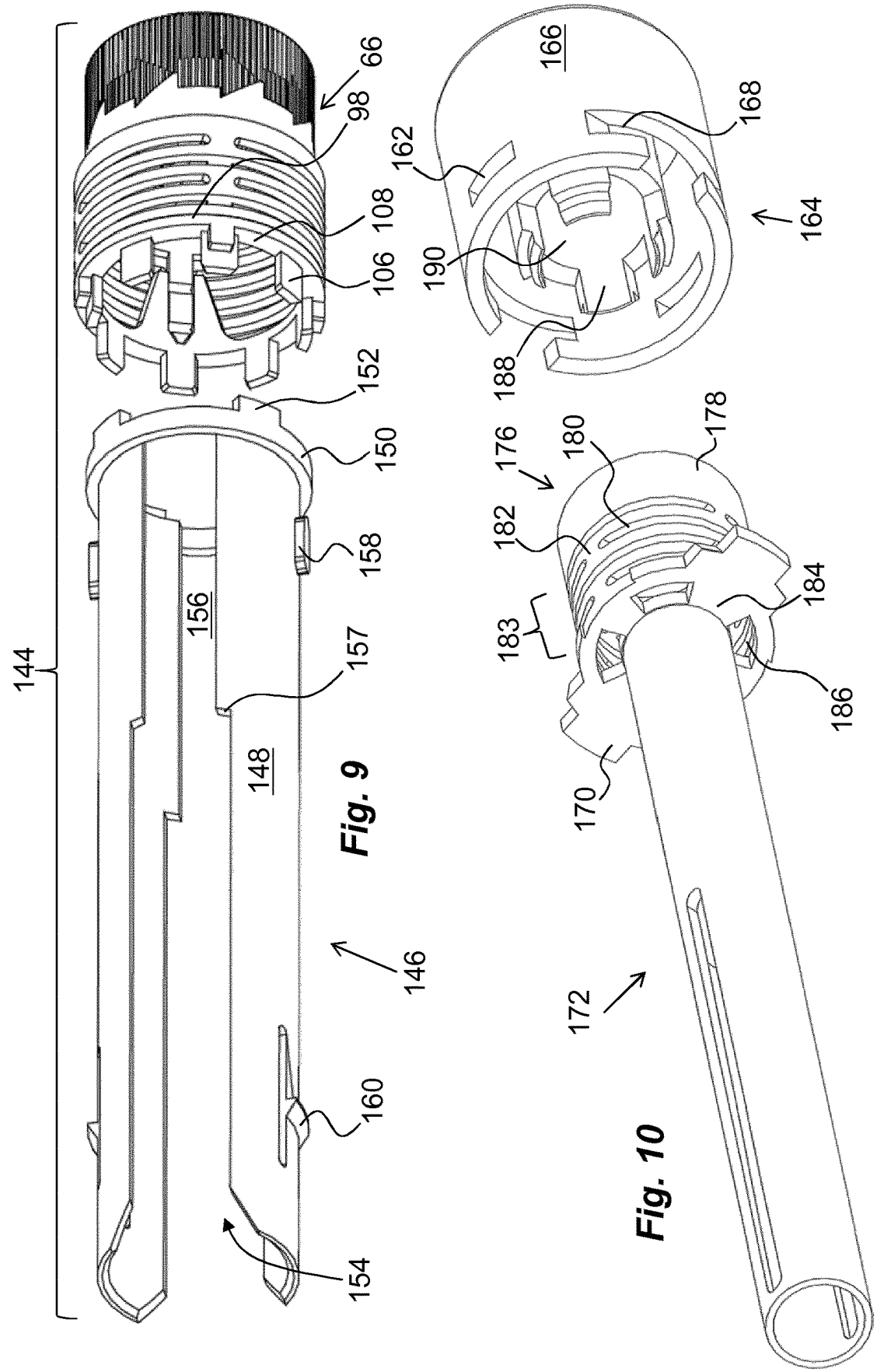

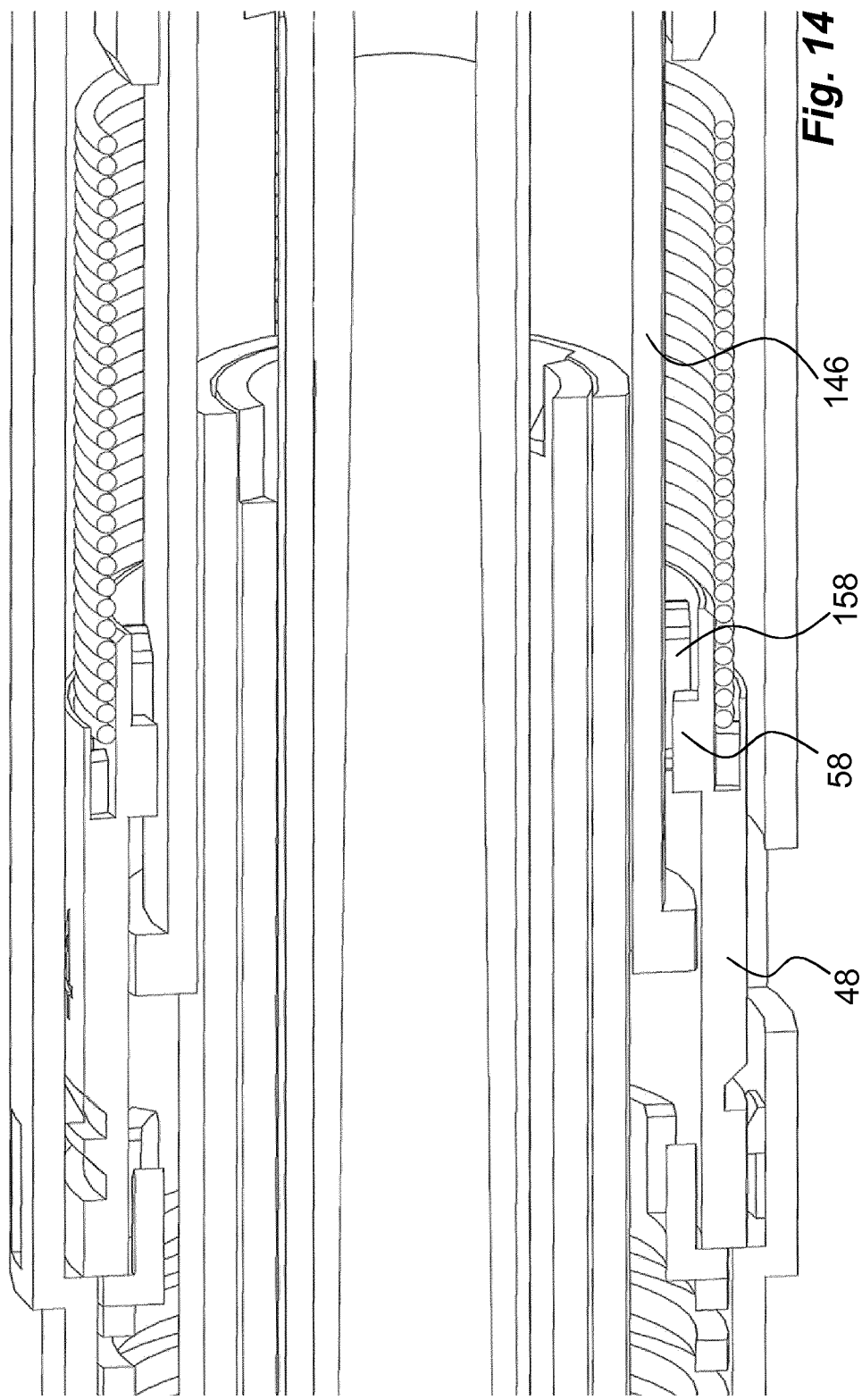

MEDICAMENT DELIVERY DEVICE

CROSS REFERENCE TO RELATED APPLICATIONS

The present application is a U.S. National Phase application pursuant to 35 U.S.C. § 371 of International Application No. PCT/EP2017/084605 filed Dec. 27, 2017, which claims priority to European Patent Application No. 17151421.9 filed Jan. 13, 2017. The entire disclosure contents of these applications are herewith incorporated by reference into the present application.

TECHNICAL AREA

The present disclosure relates to a medicament delivery device and in particular a medicament delivery device that is capable of having its length reduced during use of the device.

BACKGROUND

Many medicament delivery devices that are out on the market for self-administering of doses of medicament are arranged with dose setting features. These may be parts of the medicament delivery device that are operable in relation to other parts, such as dose drums that are rotated in relation to a housing. In some solutions the different housing parts are moved in the longitudinal direction in relation to each other when a dose is set. For instance, the document U.S. Pat. No. 5,226,896 discloses an injection pen comprising a collar and a syringe housing in threaded engagement with each other. In order to set a dose of medicament, the syringe housing is rotated in relation to the collar, whereby the syringe housing is moved inside the collar, making the housing of the device shorter.

On the other hand, when setting a dose, a distal end of the device comprising a cap attached to a distal end of a plunger rod is extended in the distal direction. This is because the proximal end of the plunger rod is in contact with a stopper in a syringe filled with medicament, and when the syringe housing is moved in the distal direction, so does the stopper, plunger rod and cap due to the incompressibility of the medicament in the syringe. Thus, the device retains more or less the same length during the setting of a dose. When then an injection is to be performed, the cap with its plunger rod is pressed manually linearly in the proximal direction by the user, causing a dose delivery.

This may be a disadvantage since the end of the movement of the plunger rod will be an indication to the user that the medicament delivery device can be safely removed from the injection site. However, due to the elastic properties of components of the medicament delivery device such as the plunger rod as well as resilient properties of the stopper possibly in combination with the viscosity of the medicament and the passage size of the injection needle, there might still be considerable pressure inside the medicament container at the end of the movement of the plunger rod. If the user now removes the medicament delivery device from the injection site, there is a pronounced risk that medicament will be expelled on the skin of the user, so called wet injection.

Further, a premature removal means that the full dose of medicament is not delivered in the medicament delivery site and the patient does not receive the full dose. Further, in many instances the user is instructed to wait a certain time period before removing the medicament delivery device from the injection site in order that the full dose is properly delivered. However, many users feel uncomfortable with injections and needles and want to remove them as quickly, or they simply forget the instructions, and then remove the medicament delivery device as soon as the plunger rod cannot be pushed any further by the user.

Regarding device size and functional features, especially regarding disposable medicament delivery devices, there are further developments to be made.

SUMMARY

In the present application, when the term "distal part/end" is used, this refers to the part/end of the device, or the parts/ends of the members thereof, which during use of the device is located the furthest away from the medicament delivery site of the patient. Correspondingly, when the term "proximal part/end" is used, this refers to the part/end of the device, or the parts/ends of the members thereof, which during use of the device is located closest to the medicament delivery site of the patient.

The aim of the present disclosure is to remedy the drawbacks of the state-of-the-art devices. This aim is obtained by a medicament delivery device according to the features of the independent patent claim. Preferable embodiments of the disclosure form the subject of the dependent patent claims.

According to one aspect of the disclosure, it comprises a medicament delivery device comprising a housing. The housing could be in one or several parts connectable to each other, depending on manufacturing aspects.

A medicament container holder is preferably provided to the housing, which may be movable in relation to the housing, which could be rotationally movable but preferably linearly movable in relation to the housing. The medicament container holder is designed to accommodate a medicament container, wherein the medicament container preferably is provided with a medicament delivery member for administering a dose of medicament.

The medicament delivery device is further arranged with an activator, wherein the activator comprises a plunger rod, preferably elongated, where the plunger rod is arranged to act on a stopper of the medicament container for delivering a dose of medicament through the medicament delivery member when the activator is operated. In this respect, the activator may be manually operated but could of course also be driven automatically by suitable drive mechanisms comprising different types of drive springs for example.

According to a favourable solution, a delay mechanism may be arranged between the activator and the plunger rod, provided with delay elements allowing movement of the activator in the proximal direction after movement of the plunger rod has terminated. With the delay mechanism the user may operate the activator even when the movement of the plunger rod has terminated. Thus, the indication to the user that the dose delivery sequence has ended is delayed by the delay mechanism. This is an advantage since the medicament delivery device is not removed prematurely precisely at the end of the dose delivery sequence which often is the case if a user receives an indication that this is the case. Remaining pressure inside the medicament container due to flexing and resilient properties of components of the medicament delivery device and the medicament container may then lead to an expelling of medicament outside the injection site, causing so called wet drooling on the skin of the user. Also, if this happens, the user will not receive the full dose of medicament.

According to one aspect of the disclosure, the delay elements may comprise resilient elements capable of exerting a resilient force between the plunger rod and the activator. In this regard, the resilient force may preferably be chosen larger than the force required to move the stopper when delivering a dose. With this solution, the activator and the plunger rod will move together until the movement of the plunger rod is terminated. After that, the resilient elements will allow the activator to be moved further during a time period until also the movement of the activator is stopped. If the resilient force of the resilient elements is chosen properly, the user will not notice the transition from moving the plunger rod and the stopper and subsequent moving of only the activator.

The resilient elements may comprise spring elements that are either an integral part of the activator or the plunger rod or a separate part positioned between the plunger rod and the activator. The material chosen may as such also display resilient properties, such as for example foam sponge material or the like. On the other hand, the resilient elements may be conventional coil springs of plastic or metal or even gas compartment that can be compressed during use.

According to one feasible solution, the delay mechanism may comprise a generally tubular body and wherein the resilient elements may comprise a number of generally circumferentially extending slits in the body with areas of material between each successive slit, forming a unit. Further, several units may be placed adjacent each other in a longitudinal direction of the tubular body, wherein areas of material of adjacent units are placed offset in the circumferential direction. With this solution, the resilient properties are "built in" in the actual design of the delay mechanism, reducing the number of components needed.

The medicament delivery device is further arranged with a manually operable dose setting member. The dose setting member may be operably connected to both the housing and the medicament container such that manual operation of the dose setting member will cause the medicament container holder with the medicament container to move towards the plunger rod for setting a dose of medicament to be delivered. The dose setting member may be rotatably connected to the housing and may further be arranged with threads that preferably are arranged on an inner surface of a passage through the dose setting member.

The threads on the dose setting member are then arranged to cooperate with threads arranged on the medicament container holder, wherein operation of the dose setting member will cause the medicament container holder with the medicament container to move towards the plunger rod for setting a dose of medicament to be delivered. When provided with threads, the dose setting member is preferably arranged rotational in the housing such that rotation of the dose setting member causes a linear movement of the medicament container holder. It is however to be understood that the dose setting member may be provided with other types of dose setting elements such that both the dose setting member and the medicament container holder are moved linearly. Alternatively the medicament container holder may be rotated for moving the medicament container to move towards the plunger rod.

A dose drum may be releasably connected to the dose setting member. Further, a releasable connection mechanism may preferably be arranged between the dose setting member and the dose drum such that when the dose setting member is operated, the dose drum may be displaced from an initial position to a set dose position. In this position, the dose setting member and the dose drum are connected and move as one unit for setting a dose. The dose drum may be arranged with indicia in order to view a set dose. In this regard, the indicia may be numbers, a number of discrete elements such as one dot or one line for position one, two lines or dots for position two, etc.

According to a favourable solution, the medicament delivery device may further comprise a release mechanism operably connected to the activator. The release mechanism is operably connected to the plunger rod such that when the plunger rod is moved to an end position of the dose delivery, the release mechanism is arranged to act on the connection mechanism for releasing the dose drum from the dose setting member. Thus when the dose delivery sequence comes to an end, the dose drum is disconnected from the dose setting member and in this position the dose setting member and the dose drum are not one unit any more but can move freely in relation to each other and in particular the dose drum can move freely.

On the other hand, according to a feasible solution, the release mechanism may be arranged with a locking mechanism arranged to lock the dose setting member from displacement as the connection mechanism is operated for releasing the dose drum from the dose setting member. Thus, in this position, the dose setting member is prevented from being operated by a user. This is an advantage in that the medicament container holder and thus the medicament container cannot be moved further now when the plunger rod is in contact with the stopper of the medicament container. If the dose setting where to be operated at this stage, it could move the medicament container holder and the medicament container such that additional medicament would be expelled through the medicament delivery member.

A further advantageous solution may be that the medicament delivery device further comprises a first resilient member arranged between the dose drum and the housing, which first resilient member is tensioned when a dose is set by operating the dose setting member such that the dose drum is displaced from the initial position to the set dose position, and is capable of moving the dose drum back from the set dose position to the initial position when the dose drum is released from the dose setting member. Thus, with this solution, the dose drum is automatically moved to the initial position in contrast to a manual operation by a user for resetting the dose drum.

According to one solution, the connection mechanism may comprise protrusions operably connected to one of the dose setting member or dose drum engageable with cut-outs on the other of the dose drum or dose setting member. The protrusions may be arranged to display resilient properties in order to obtain a releasable connection. In this regard, according to the embodiment shown, a section of the dose setting member that is facing the dose drum is arranged with resilient elements providing resiliency in a longitudinal direction. The protrusions could then either be integral with the dose setting member, or provided on a separate component. Resilient protrusions provide a releasable connection between the dose drum and the dose setting member. The resiliency may be created in many ways. Either the protrusions as such are made of a resilient material. It may also be that the protrusions are attached to or integrated with elements that display resilient properties such as arms that are bendable. Further, the resiliency may be obtained by springs.

The release mechanism may further comprise a release sleeve and the locking mechanism may comprise a number of protrusions on one of the dose setting member or release sleeve engageable with a number of cut-outs on the other of the release sleeve or dose setting member. Also here the protrusions may be resiliently arranged and the resiliency may be obtained as described above. On the other hand, the protrusions may be arranged to one and the same resilient element, such as a resilient arm. Then the protrusions may protrude to different extents and/or different directions so as to cause a release of the dose drum at the same time as the dose setting member is locked. This solution provides a compact function with very few components.

According to another aspect of the disclosure, the release mechanism may further comprise rotational locking elements arranged to lock the dose drum and the dose setting member during delivery of the dose. This may be important so that the dose size may not be manipulated, intentionally or by accident, during the dose delivery sequence. Thus only a linear movement of the activator with the plunger rod as well as the release mechanism is allowed during this stage. In this respect, in order to allow rotation of the dose drum at the end of the dose delivery sequence, the rotational locking elements are arranged to release the dose drum and the dose setting member.

According to one aspect in this regard, the rotational locking elements may as an example comprise longitudinally extending grooves on one of the release mechanism and the dose drum, arranged to cooperate with longitudinally extending ribs on the other of the release mechanism and the dose drum. It is however possible to have other solutions preventing rotation, such as ribs acting on ribs, discrete protrusions sliding along ribs or ledges, just to mention a few.

According to a further aspect, the dose setting member may comprise a number of locking elements configured to interact with at least one corresponding locking element of the medicament container holder for releasably locking rotational positions of the dose setting member during setting of a dose. This has several advantages in that it provides the user with distinct dose size positions, which positions may correspond to certain indicia on the dose drum that are visible to the user during the setting of a dose. Also, when a first resilient member is used for moving the dose drum back to the initial position, when the dose setting member and the dose drum are connected as one unit during dose setting, the spring will act on both components, trying to move them back to the initial position. The dose setting member locking elements will then maintain the set position of the unit despite the force of the first resilient member.

In this regard, the dose setting member locking elements may comprise protrusions on an inner surface of the dose setting member cooperating with recesses on an outer surface of the medicament container holder. Further, the combination could be the other way around. Further, with this solution, the dose setting member locking elements will provide tactile and audible information during setting of a dose in that the protrusions will move in and out of engagement with the recesses or grooves causing sudden movement of the protrusions which will give rise to sound as well as vibrations.

Further, the medicament delivery device may comprise a dose limiting mechanism operably arranged to the dose drum and capable of limiting the maximum dose to be set so that a user cannot set a dose size that cannot be handled or delivered by the medicament delivery device. According to one possible solution, the dose limiting mechanism comprises a groove extending a distance along the circumference of the dose drum arranged to interact with a stop ledge on the housing, wherein the turning of the dose setting member will bring the stop ledges in contact with the end of the groove within one turn of the dose setting member, limiting the maximum dose to be set. It is however to be understood that other types of solutions are possible within the desired function. For instance the groove may be replaced with discrete protrusions at each desired stop position, wherein the stop ledge on the housing only comes in contact with the dose drum when it abuts one of the protrusions.

Preferably the medicament delivery device further comprises a rotational lock arranged between the medicament container holder and the housing wherein the medicament container holder can only move linearly when the dose setting member is rotated. The rotational lock may be comprising at least one elongated band on the outer surface of the medicament container holder fitting into a cut-out in the housing. Further the at least one elongated band may be arranged with threads that cooperate with the threads of the dose setting member. In order to have an equal distribution of forces on the medicament container holder when the dose setting member is rotated for setting a dose, at least two elongated bands should be provided on opposite sides of the medicament container holder.

Further a last dose mechanism may be arranged, which is operably arranged to the dose setting member and capable of limiting the maximum dose to be set to the remaining quantity of medicament in the medicament container. As one feasible solution, the last dose mechanism may comprise a stop ledge in a proximal area of the medicament container holder, arranged to come in contact with, and limit the movement, of the dose setting member.

According to one feasible solution the activator may comprise a manually operable push button extending in a distal direction through the housing. The push button may have an end wall acting as a pushing surface for a user. On the proximal side of the end wall, the plunger rod may be attached or made integral. Since the device is intended to be used several times giving several doses of medicament before being discarded, the activator may comprise a return force element arranged to return the activator after delivery of a dose of medicament. The activator is then ready for a subsequent dose delivery sequence.

These and other aspects of, and advantages with, the present disclosure will become apparent from the following detailed description of the disclosure and from the accompanying drawings.

BRIEF DESCRIPTION OF DRAWINGS

In the following detailed description of the disclosure, reference will be made to the accompanying drawings, of which

FIG. 3 is a detailed view of components comprised in the embodiment of FIG. 1;

FIG. 4 is a detailed view of components comprised in the embodiment of FIG. 1;

FIG. 9 is a detailed view of components comprised in the embodiment of FIG. 1;

FIG. 10 is a detailed view of components comprised in the embodiment of FIG. 1;

FIG. 14 is a cross-sectional view showing a different functional position;

DETAILED DESCRIPTION

Figure 1:
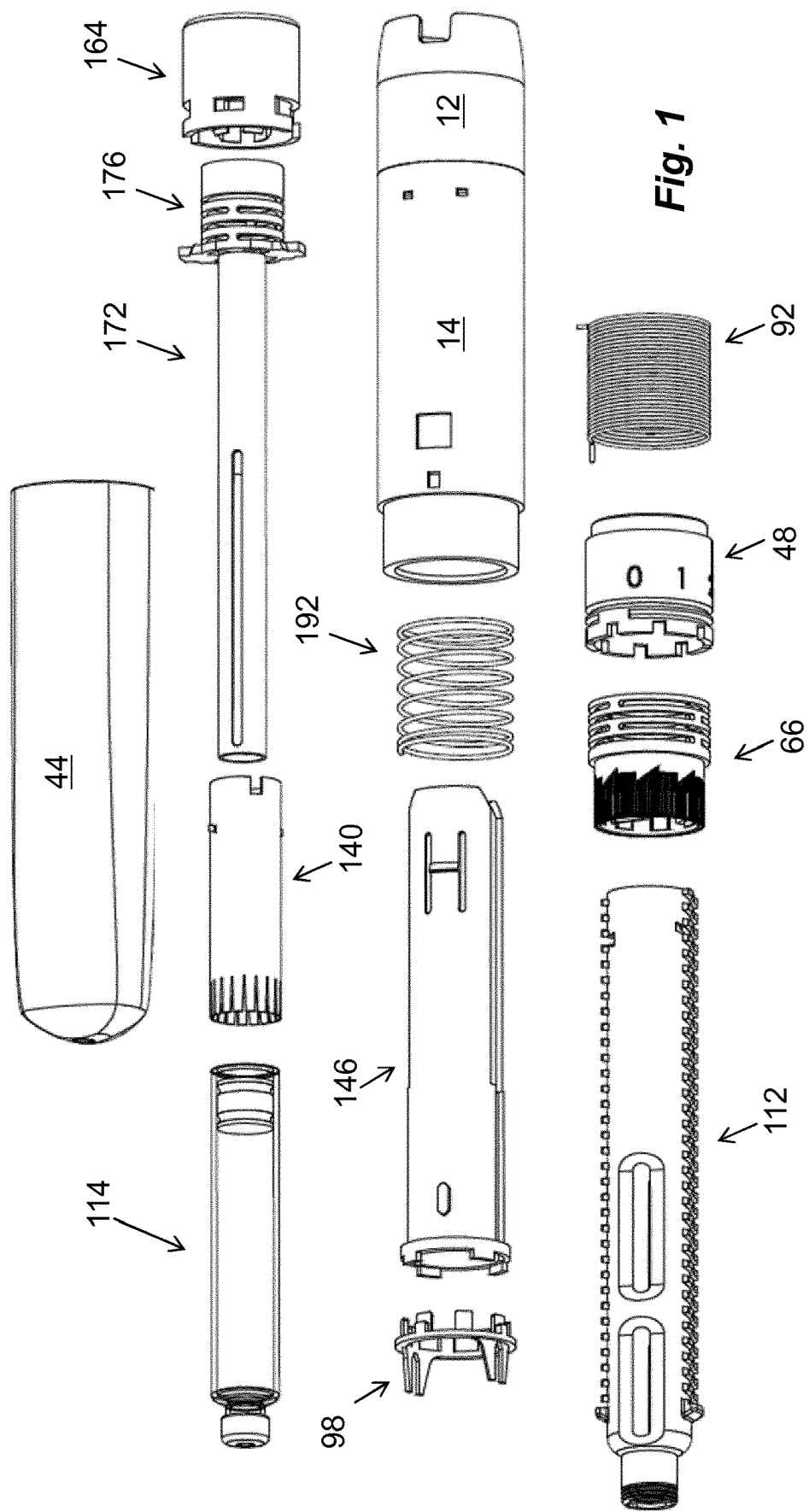
FIG. 1 is an exploded view of one embodiment of the present disclosure.

The embodiment of a medicament delivery device 10 shown in the drawings comprises a generally tubular housing that in the embodiment shown is in a distal housing part 12 and proximal housing part 14. The distal housing part 12 is arranged with a first proximal area 16, FIG. 4, having a diameter somewhat smaller than the rest of the housing part, creating a proximally directed circumferential ledge 18. The first proximal area 16 is further arranged with a number of outwardly directed longitudinal protrusions 20. The protrusions 20 are arranged to fit into longitudinal grooves 22 on an inner surface of the proximal housing part 14 at its distal end, FIG. 5, providing a rotational lock between the housing parts. The protrusions 20 are further arranged with outwardly directed ledges 24, which ledges 24 are arranged to be snap-fitted into recesses 26 in the longitudinal grooves 22, such that the two housing parts are connected to each other with a distal part of the proximal housing part 14 covering the proximal area 16 and with a distal end surface in contact with the proximally directed ledge 18.

Figure 5:
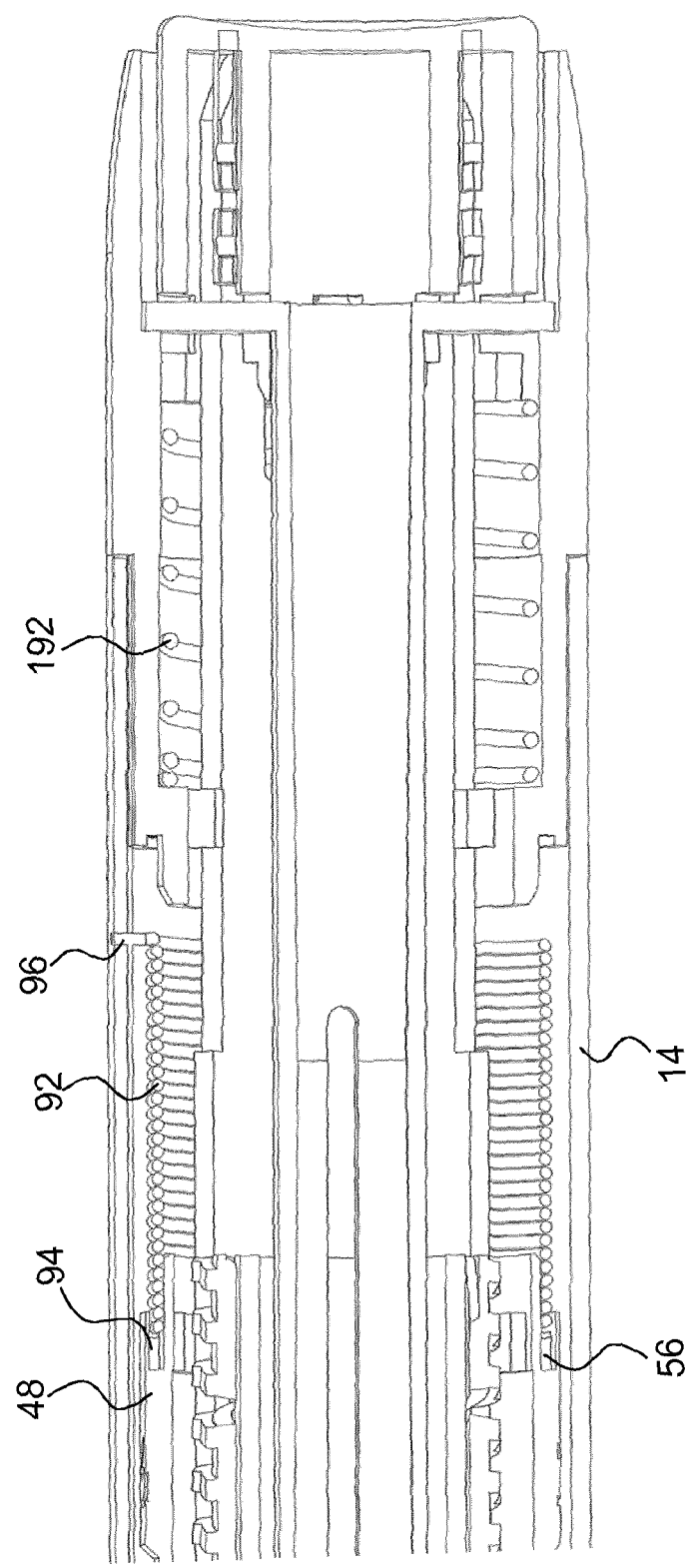
FIG. 5 is a detailed view of components comprised in the embodiment of FIG. 1.

The distal housing part 12 is provided with a distally directed passage 28, FIG. 3b, and is further arranged with an annular ledge 30, which ledge 30 is provided with a number of recesses 32, FIG. 5, on its proximally directed surface. The annular ledge 30 is further arranged with radially inwardly directed guide ledges 34, FIG. 5, the function of which will be described below.

The proximal housing part 14 is provided with an inwardly directed protrusion 36. In a passage 37 at the proximal end of the proximal housing part 14, an annular inwardly directed ledge 38 is arranged. The proximal end of the proximal housing part 14 is further arranged with an area 40, FIG. 4, with somewhat reduced diameter than the rest of the proximal housing part, creating a proximally directed ledge 42. The area 40 is intended to accommodate a distal end of a protective cap 44, FIG. 1, wherein a distal end surface of the protective cap 44 is abutting the ledge 42. The proximal housing part is further arranged with an opening or window 46, FIG. 4.

Figure 6:
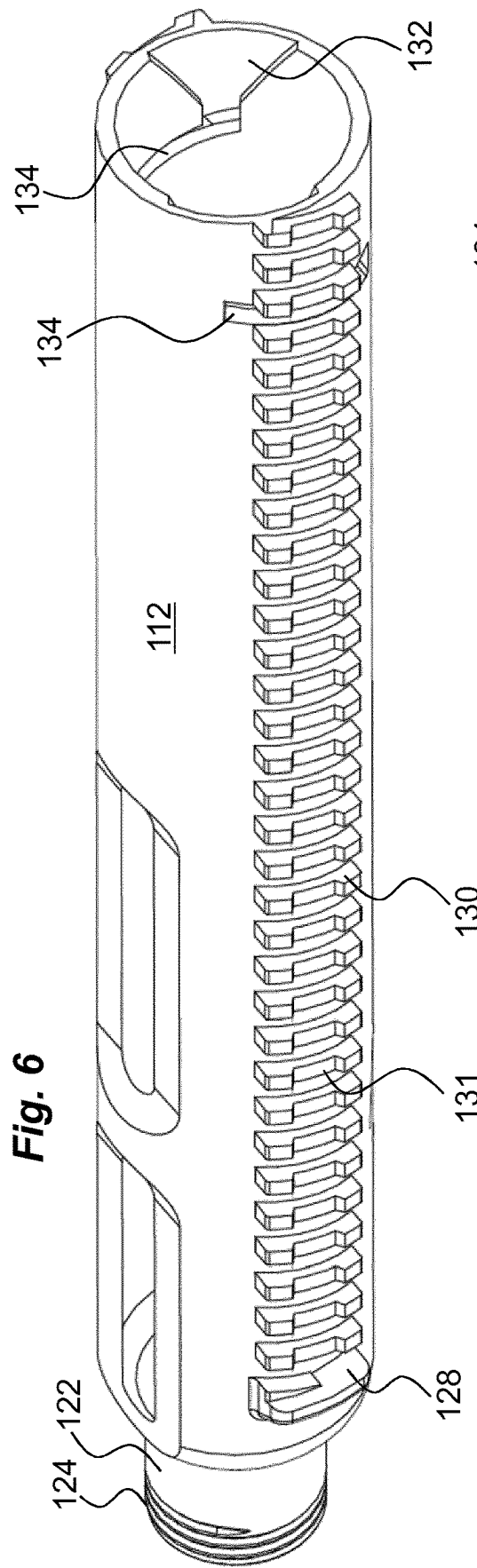
FIG. 6 is a detailed view of components comprised in the embodiment of FIG. 1.
Figure 7:
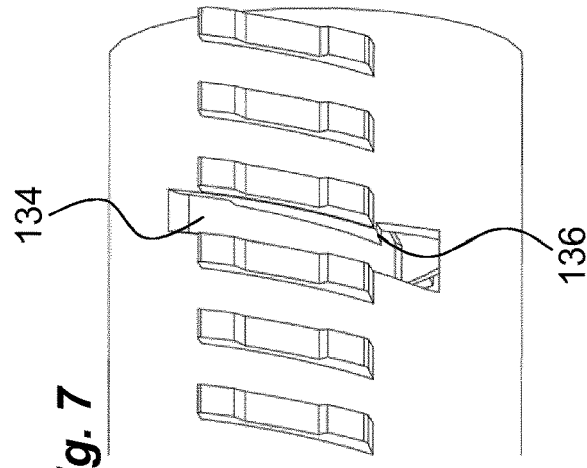
FIG. 7 is a detailed view of components comprised in the embodiment of FIG. 1.

The medicament delivery device 10 is further provided with a generally tubular dose drum 48, FIGS. 6 and 7. The outer diameter of the dose drum 48 is somewhat smaller than the inner diameter of the proximal housing part 14 so that the dose drum 48 may be placed inside and coaxial with the proximal housing part 14. The outer surface of the dose drum 48 is arranged with a groove 50, FIG. 6, extending in a circumferential direction on the outer surface of the dose drum 48. The groove 50 does not extend the full circumference but is interrupted by a bridging area 52. The inwardly directed protrusion 36 of the proximal housing part 14 is intended to fit into the groove 50 of the dose drum 48. The protrusion 36 and the groove 50 enables turning of the dose drum 48 in relation to the proximal housing part 14 almost a full turn, stopped by the bridging area 52, and preventing axial relative movement.

The distal area of the dose drum 48 is arranged with an annular ledge 54, wherein a distally directed surface of the ledge 54 is provided with a number of recesses 56. An inner surface of the ledge 54 is provided with a number of annularly extending protrusions 58 separated by cut-outs 60. Further, the dose drum 48 has a proximally directed end surface 61, which end surface 61 is arranged with generally rectangular cut-outs 62 around its circumference, comprised in a connection mechanism. Also, the outer surface of the dose drum 48 is arranged with indicia 64 such as numbers, which indicia 64 are shown in the opening or window 46 in the proximal housing part 14.

Adjacent the dose drum 48 a generally tubular dose setting member 66 is arranged, FIGS. 6 and 7. The dose setting member 66 is arranged with a proximal part 68 having a diameter somewhat smaller than the diameter of the passage 37 of the proximal housing part 14. The dose setting member is further arranged with a distal part 70 of a larger diameter, thereby creating an annular ledge 72 at its distal end. The dose setting member is intended to extend with its proximal part through the passage 37 and with its ledge 72 in contact with a distal surface of the annular ledge 38, limiting the movement in the longitudinal proximal direction of the dose setting member 66 in relation to the proximal housing part 14.

The outer surface of the proximal part 68 of the dose setting member 66 that is extending through the proximal housing part 14 is preferably arranged with grip elements such as grooves 74 providing a grip surface. The grip surface of the dose setting member 66 may also be arranged with indicia such as arrows 78, providing information to a user which direction the dose setting member 66 should be rotated, as will be described below.

The distal part 70 is arranged with a number of successive slits 80 that extend in the circumferential direction where the slits are separated by areas of material 82. The slits are positioned such that adjacent areas of material 82 of sets of slits 80 are placed offset in the circumferential direction which provides a resilient function of the distal part 70 in a longitudinal direction. Further longitudinally extending protrusions 84 are positioned on the inner surface of the distal part 70. The dose setting member 66 is on an inner surface of a central passage 86 of the proximal part 68 provided with thread segments 88. Further a number of annularly extending protrusions 90 are positioned on the inner surface adjacent the thread segments 88.

Figure 8:
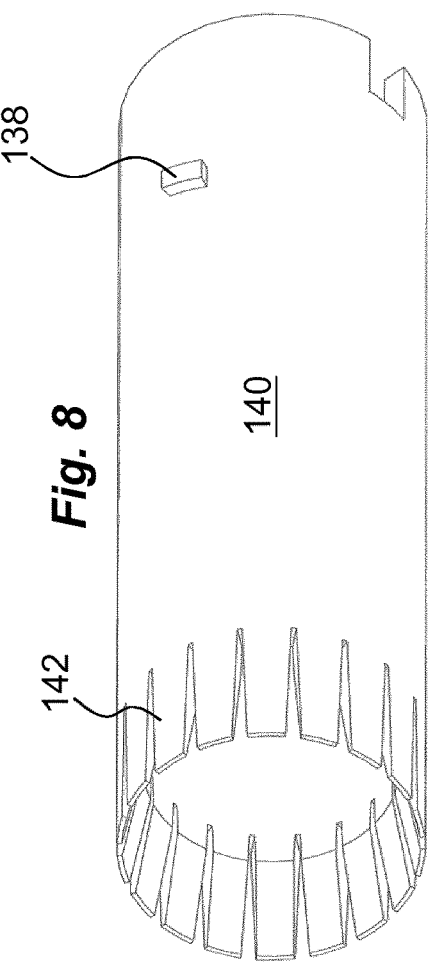
FIG. 8 is a detailed view of components comprised in the embodiment of FIG. 1.

A first resilient member 92, FIGS. 1 and 8, which is a torsion spring in the presented embodiment, hereafter named dose drum spring, is arranged coaxial with the proximal housing part 14 and having a proximal end 94 of the dose drum spring 92 seated in the recesses 56 of the dose drum 48 and a distal end 96 of the dose drum spring 92 seated in a passage in the proximal housing part 14 as seen in FIG. 7.

A connection member 98 is further arranged to the dose setting member 66, FIG. 4. It comprises a generally ringshaped body 100 having a diameter generally corresponding to the diameter of the distal part. The body 100 is provided with proximally directed arms 102, which arms 102 are arranged with slits 104, wherein the protrusions 84 of the distal part 70 of the dose setting member 66 are designed to fit into the slits 104 of the arms 102, forming a rotational lock. At the distal end of the body 100 a number of distally directed, generally rectangular, first protrusions 106 are provided equidistant around the circumference with rectangular cut-outs 108 between the first protrusions 106. On every second of the first protrusions 106, a second protrusion 110 is placed radially outside, the function of which will be explained below.

Figure 2A:
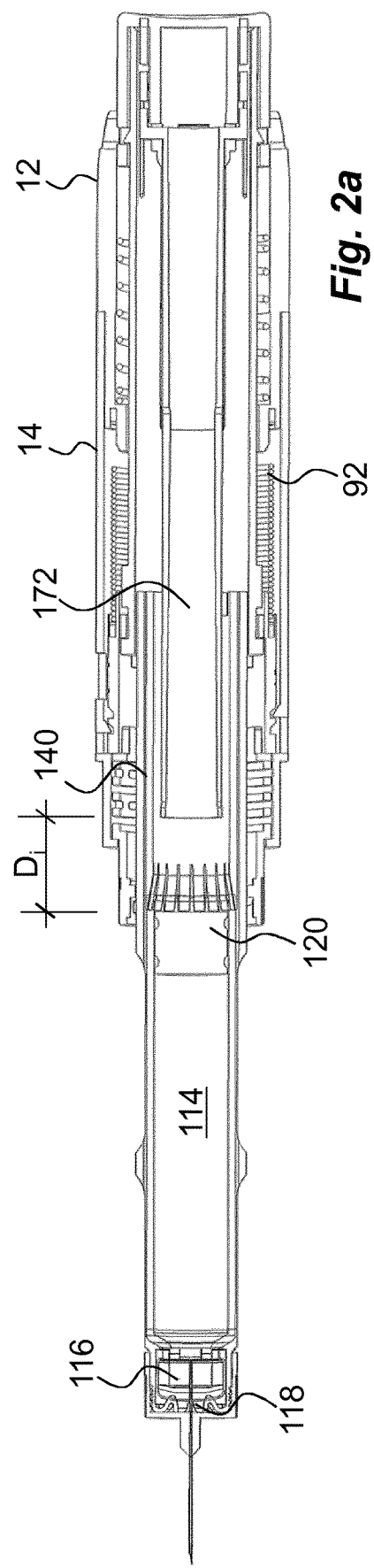
FIG. 2 is a longitudinal cross-section of the medicament delivery device of FIG. 1.
Figure 2B:
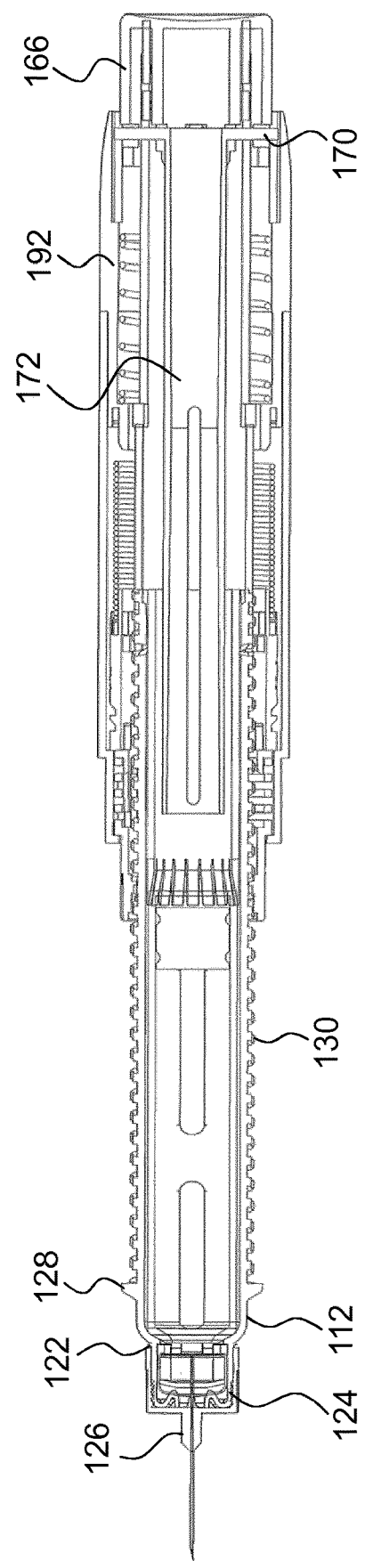

The medicament delivery device 10 is further arranged with a generally tubular, elongated, medicament container holder 112, FIGS. 1 and 9, which is arranged to fit into the housing parts via the central passage 86 in the dose setting member 66. The medicament container holder 112 is designed to accommodate a medicament container 114, which medicament container 114 is arranged with a neck portion 116, FIG. 2, in turn arranged with a penetrable septum 118. Further a stopper 120 is arranged movable inside the medicament container 114, FIG. 2. When fitted into the medicament container holder 112, its neck portion 116 fits into a proximal neck portion 122 of the medicament container holder 112 as seen in FIG. 2b. The neck portion 122 of the medicament container holder 112 is arranged with attachment elements 124 for releasably attaching a medicament delivery member 126, in the embodiment shown an injection needle. The attachment elements 124 may be threads as shown, but may instead be of other types, such as bayonet fittings, luer connection etc. Radially outwardly directed protrusions 128 are further arranged on an outer surface of the medicament container holder 112 at a proximal area thereof.

The medicament container holder 112 is arranged with two elevated bands of thread segments 130 on its outer surface, on opposite sides thereof. The thread segments 130 are arranged to cooperate with the thread segments 88 of the dose setting member 66 as will be described. Further the bands of thread segments 130 are designed to fit between the inwardly directed guide ledges 34 of the distal housing part 12, thereby providing support and guidance of the medicament container holder 112 in the longitudinal direction as well as preventing rotation of the medicament container holder 112 in relation to the housing parts. Each thread segment of the bands of thread segments 130 is arranged with a recess 131, FIGS. 9 and 14, into which recesses 131 the protrusions 90 of the dose setting member 66 can be releasably positioned as will be described below. At the distal end of the medicament container holder 112 on its inner surface a narrowing recess 132 is provided, FIG. 9, leading to a cut-out 134 in the form of a slit extending generally in the same direction as the thread segments on the outer surface as seen in FIGS. 9 and 10. The end of the slit 134 is arranged with a ledge 136. The slit 134 is intended to function together with protrusions 138 on an outer surface of a generally tubular medicament container fixator 140, FIG. 8, wherein the proximal end of the medicament container fixator 140 is provided with bevelled flexible tongues 142, that are intended to press against the distal end of the medicament container 114 when the protrusions 138 are sliding in the slits 134 of the medicament container holder 112. The medicament container 114 is locked when the protrusions 138 enter the ledge 136 of the slits 134.

Figure 12:
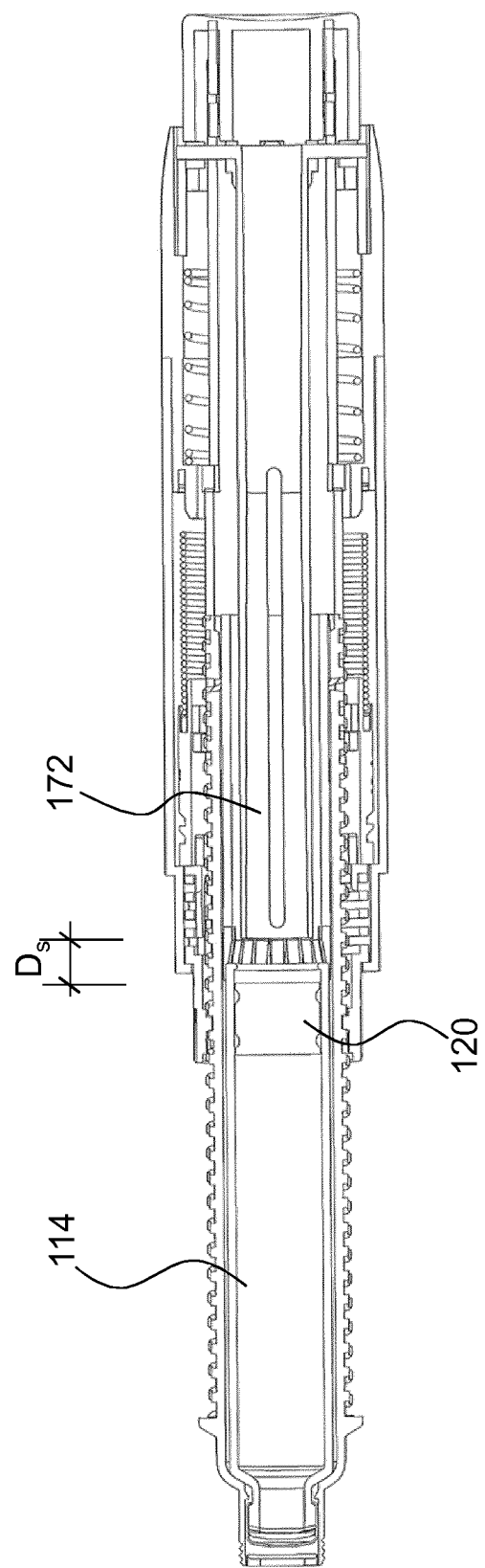
FIG. 12 is a cross-sectional view showing a different functional position.

Further, a release mechanism 144, FIG. 12, is arranged in the medicament delivery device 10. It comprises a release sleeve 146, FIG. 12, having a generally tubular body 148, which body 148 is provided with an annular ledge 150 at a proximal end. The ledge 150 of the release sleeve 146 is provided with proximally directed protrusions 152 that are intended to cooperate with the distally directed protrusions 106 of the connection member 98 as will be described.

The release sleeve 146 has a passage 154 with a diameter somewhat larger than the diameter of the medicament container holder 112, where the latter extends into the passage 154. The passage 154 is further arranged with longitudinal cut-outs 156 in which the bands of thread segments 130 of the medicament container holder 112 fit, creating a rotational lock between the medicament container holder 112 and the release mechanism 144. The longitudinal cut-outs 156 are further arranged with distally directed ledges 157, which ledges 157 are intended to cooperate with the guide ledges 34 of the distal housing part 12 as will be described.

The release sleeve 146 is arranged with a number of longitudinally extending protrusions 158 on its outer surface, which protrusions are to interact with the protrusions 58 and the cut-outs 60 of the dose drum 48 as will be described.

At the distal end of the release sleeve 146 two wedge-shaped outwardly extending protrusions 160 are arranged on opposite sides. These protrusions 160 are intended to fit into recesses 162 in an activator 164, FIG. 13 9, which activator 164 has a generally tubular body 166. The distal end of the activator 164 is intended to extend through the passage 28 of the distal housing part 12 so that it is accessible for a user as will be described. The body 166 of the activator 164 is further arranged with generally rectangular cut-outs 168. The cut-outs 168 are designed to accommodate plate-like guide elements 170 that extend radially out from a generally tubular elongated plunger rod 172. Further, the outer ends of the guide elements 170 are designed to fit into longitudinally extending grooves 174 on the inner surface of the distal housing part 12 adjacent the passage 28, FIG. 5.

Further, at the distal end of the plunger rod 172 a delay mechanism 176 is arranged. It comprises a generally tubular body 178 provided with successive slits 180 that extend in the circumferential direction where the slits are separated by areas of material 182. The slits 180 are positioned such that adjacent areas of material 182 of sets of slits 180 are placed offset in the circumferential direction which provides a section 183 with resilient functions of the distal part in a longitudinal direction. The inner area of the delay mechanism 176 is arranged with a seat 184 in which a number of passages 186 are provided. These passages 186 are arranged to cooperate with proximally directed protrusions 188 on a central hub 190 of the activator, wherein the hub 190 has an outer diameter generally corresponding to the inner diameter of the tubular body 178.

A second resilient member 192, FIGS. 1 and 8, which is a compression spring in the present embodiment, hereafter named activator return spring, is arranged between a proximally directed end surface of the body 166 of the activator 164 and the distally directed surface of the annular ledge 30 of the distal housing part 12.

The device is intended to function as follows. The medicament delivery device is preferably delivered with a medicament container 114 in the medicament container holder 112 and fixated by the medicament container fixator 140. When the user is to administer a dose of medicament, the protective cap 44 is removed. For setting a dose the dose setting member 66 is rotated in relation to the housing 12, 14. Because of the threaded connection between the dose setting member 66 and the medicament container holder 112 by the thread segments 88 of the dose setting member 66 engaging the bands of thread segments 130 of the medicament container holder 112, the medicament container holder 112 will move, together with the medicament container 112, in the distal direction. The second outer protrusions 110 of the connection member 98 are in engagement with the cut-outs 62 of the dose drum 48. The connection member 98 is further in rotational lock with the dose setting member 66 via the protrusions 84 in engagement with the slits 104, whereby the connection member 98 and the dose drum 48 will also rotate when the dose setting member 66 is rotated. The indicia 64 on the dose drum 48 will be displayed through the window 46, indicating the set dose.

Figure 11:
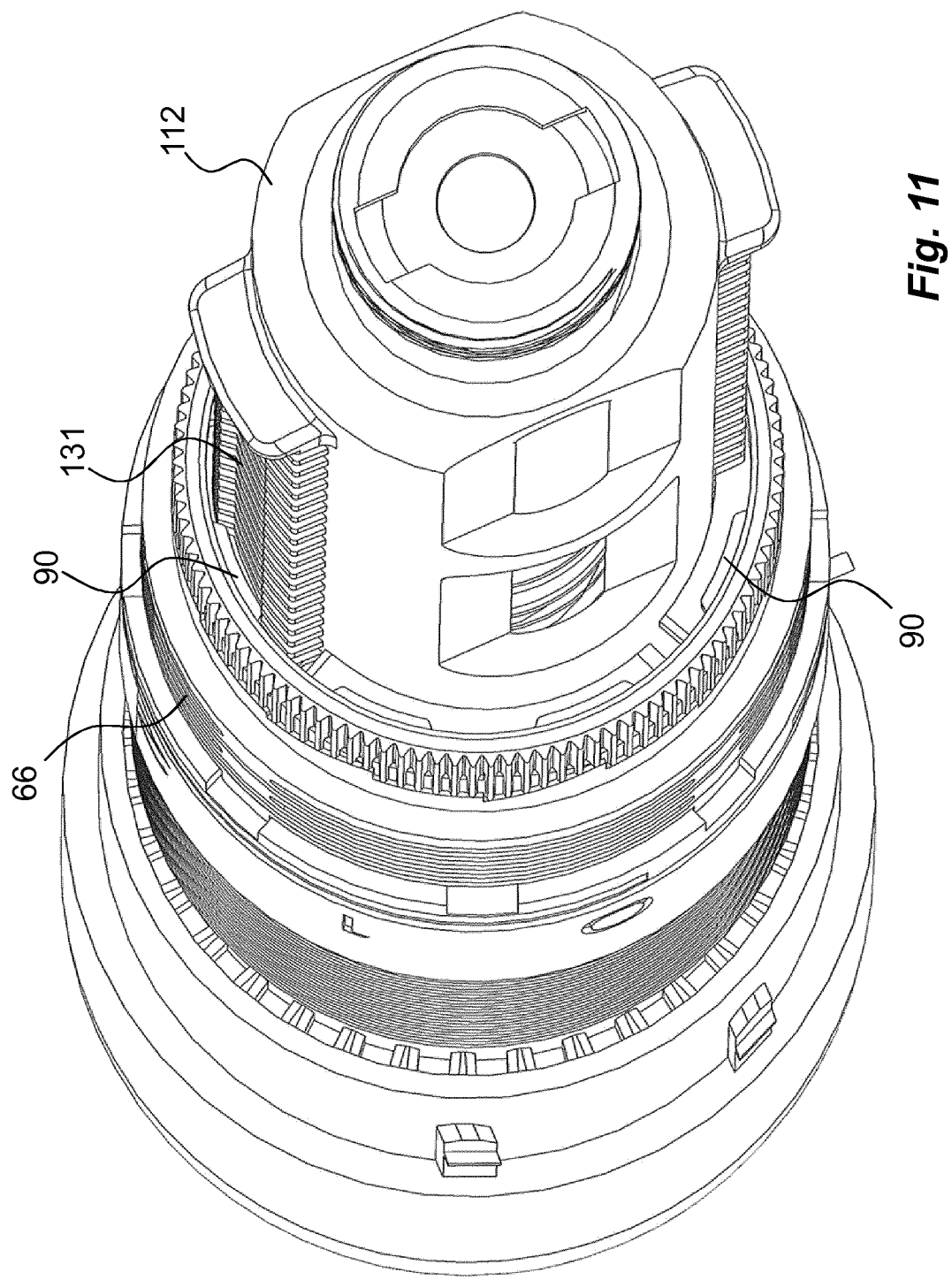
FIG. 11 is a detailed view of components comprised in the embodiment of FIG. 1.

As the dose drum 48 rotates the dose drum spring 92 will be tensioned because the proximal end 94 of the dose drum spring 92 is in engagement with the recesses 56 of the dose drum 48 and the distal end 96 of the dose drum spring 92 is in engagement with the proximal housing part 14. During the setting of the dose by turning the dose setting member 66, the inwardly directed protrusions 90 on the inner surface of the dose setting member 66 will move in and out of the recesses 131 of the bands of thread segments 130, FIG. 11, due to the flexing properties of the material of the dose setting member 66, causing an audible and tactile response. The protrusions 90 placed in the recesses 131 will also hold the dose setting member 66 and thus the dose drum 48 in a set position against the force of the dose drum spring 92.

The maximum dose to be set is limited by the groove 50 of the dose drum 48 and the inwardly directed protrusion 36 of the proximal housing part 14 in that the inwardly directed protrusion 36 will come in contact with the end of the groove 50 when the dose drum 48 has been rotated a certain distance, which is less than a full turn. However, within this rotational range, it is possible to turn up and down the dose size as desired by the user.

Figure 15:
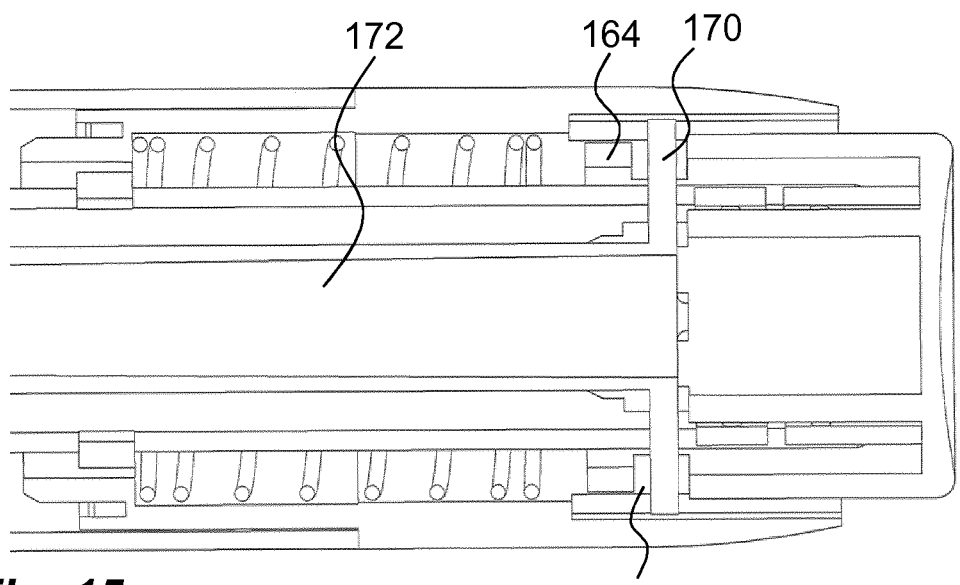
FIG. 15 is a cross-sectional view showing a different functional position.
Figure 16:
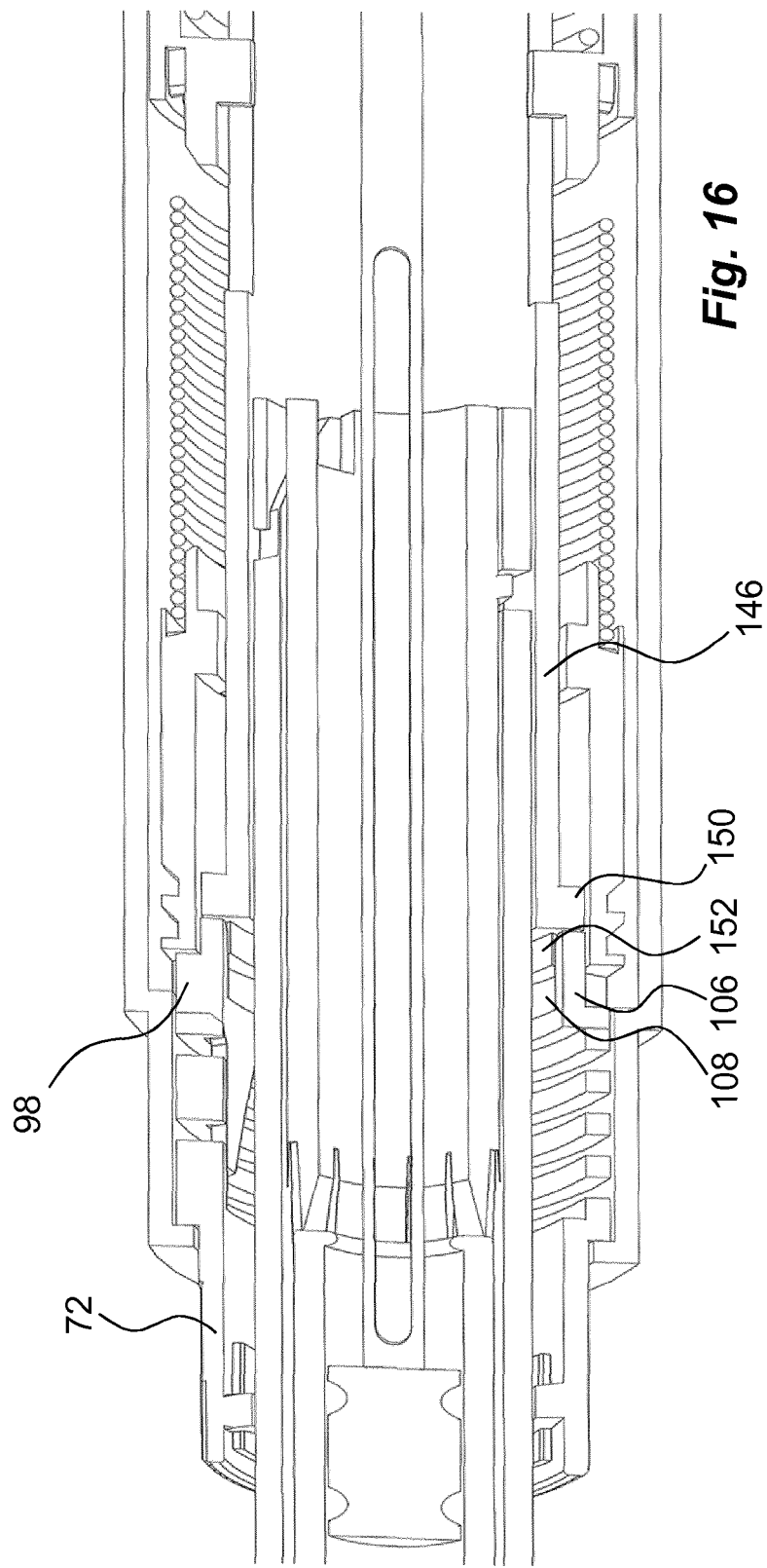
FIG. 16 is a cross-sectional view showing a different functional position.
Figure 17:
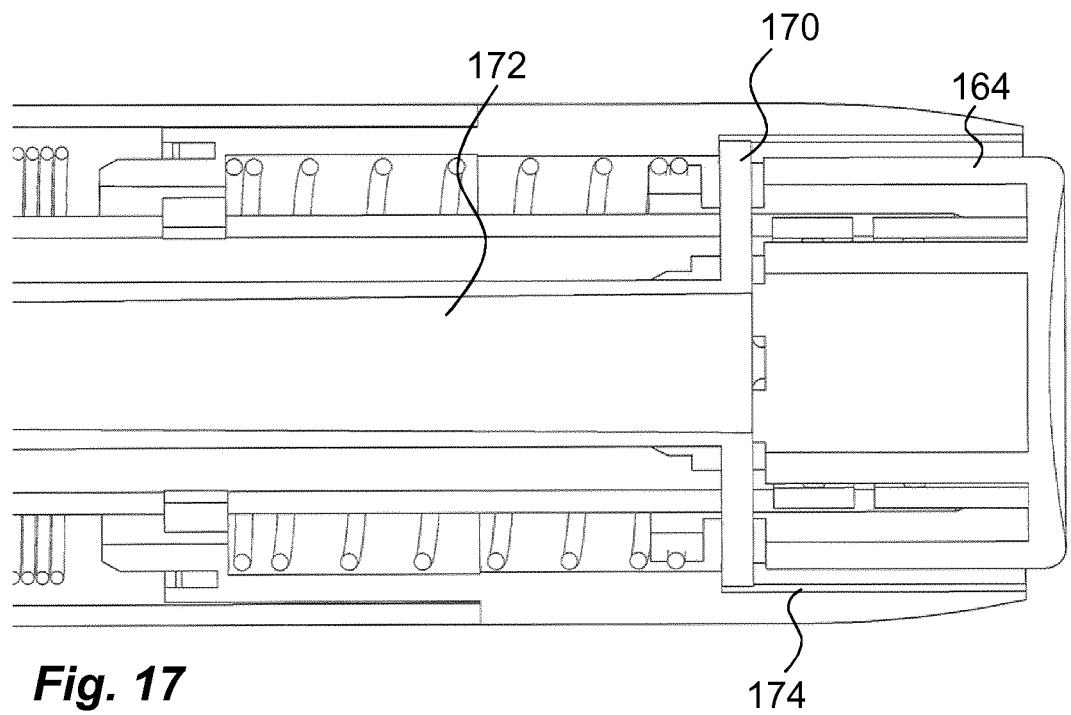
FIG. 17 is a cross-sectional view showing a different functional position.
Figure 18:
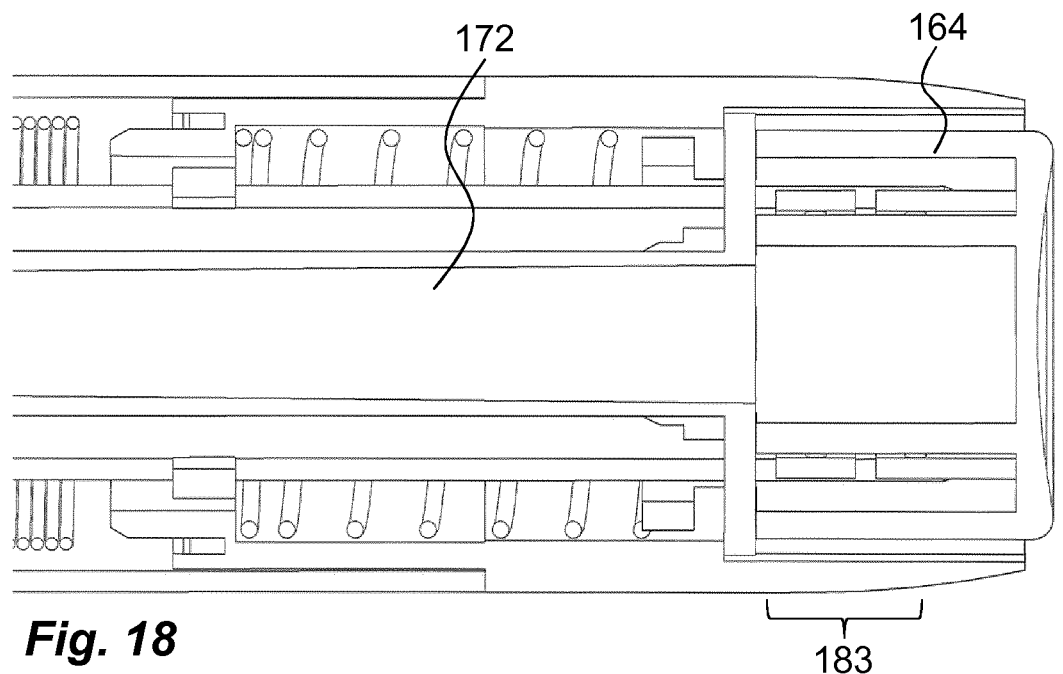
FIG. 18 is a cross-sectional view showing a different functional position.
Figure 19:
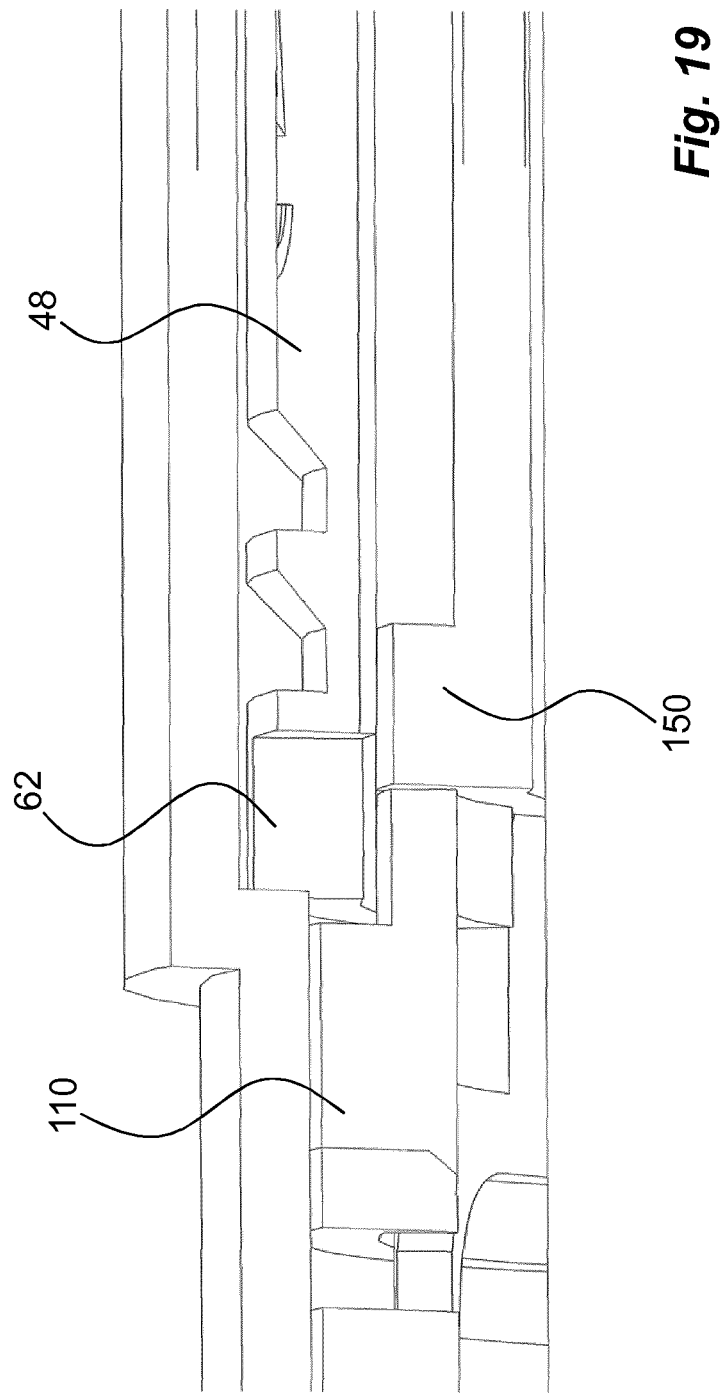
FIG. 19 is a cross-sectional view showing a different functional position.

It is further to be noted that the plunger rod 172 is designed and positioned such in an unaffected initial position that its proximal end does not come in contact with the stopper 120 of the medicament container 114 even when a maximum dose has been set, in which position the medicament container holder 112 and the medicament container 114 have been moved a maximum distance in the distal direction. FIG. 15 shows a set dose when the medicament container holder 114 and the medicament container 112 have moved distally from an initial position with a distance $D_i$ between the distal end surface of the stopper and the proximal end of the plunger rod in FIG. 2 to a set position with a distance $D_s$ as seen in FIG. 15. Also, as seen in FIG. 16, before use of the activator, the plunger rod 172 is pushed in the proximal direction in relation to the activator 164 by the resilient section of the delay mechanism 176 whereby the guide elements 170 of the plunger rod 172 are in contact with distally directed surfaces of the cut-outs 168 in the activator 164.

When the dose has been set, a medicament delivery member 126 is attached to the neck portion 122 of the medicament container holder 112. In the embodiment shown in FIGS. 2 and 3, the medicament delivery member 126 is an injection needle that is screwed onto the neck portion 122. The injection needle is then arranged with a distally directed pointed end that will penetrate the septum 118 of the medicament container 114. The user then places the medicament delivery device at the dose delivery site, causing a penetration of the injection needle. The tubular body 166 of the activator 164 is then pressed in the proximal direction by the user against the force of the activator return spring 192. First, the plunger rod 172 will be moved proximally the distance $D_s$ without being in contact with the stopper 120 of the medicament container 114, where the distance is dependent on the set dose, wherein a larger dose will provide a shorter distance and a smaller dose a larger distance.

During the movement of the activator 164 in the proximal direction the release sleeve 146 is also moved in the proximal direction due to the connection with activator 164. The movement of the release sleeve 146 in the proximal direction will cause the protrusions 158 of the release sleeve 146 to be moved in engagement with the cut-outs 60 between the protrusions 58 on the inner surface of the dose drum 48, thereby locking the dose drum 48 from rotation, FIG. 12.

Figure 13:
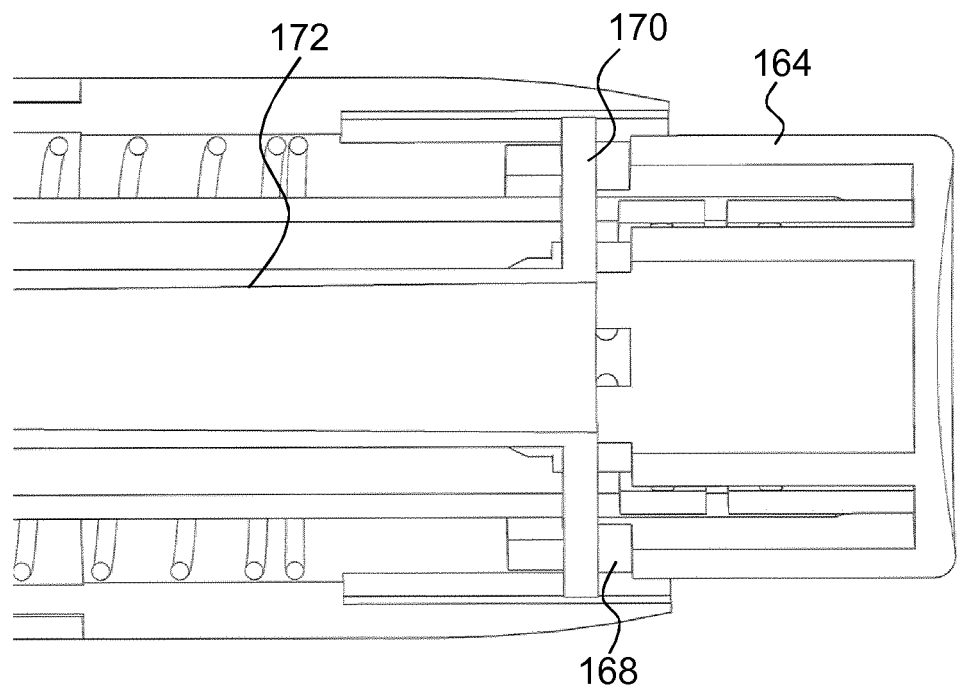
FIG. 13 is a cross-sectional view showing a different functional position.

When the plunger rod 172 has moved this distance, it comes in contact with the stopper 120 and pushes it in the proximal direction, causing delivery of the set dose of medicament through the medicament delivery member 126. The resilient section 183 of the delay mechanism 176 will be somewhat compressed as seen in FIG. 13, wherein the guide elements 170 have been moved out of contact with the activator 164. However, during dose delivery, the guide elements 170 slide in the longitudinally extending grooves 174 of the distal housing part.

Figure 20:
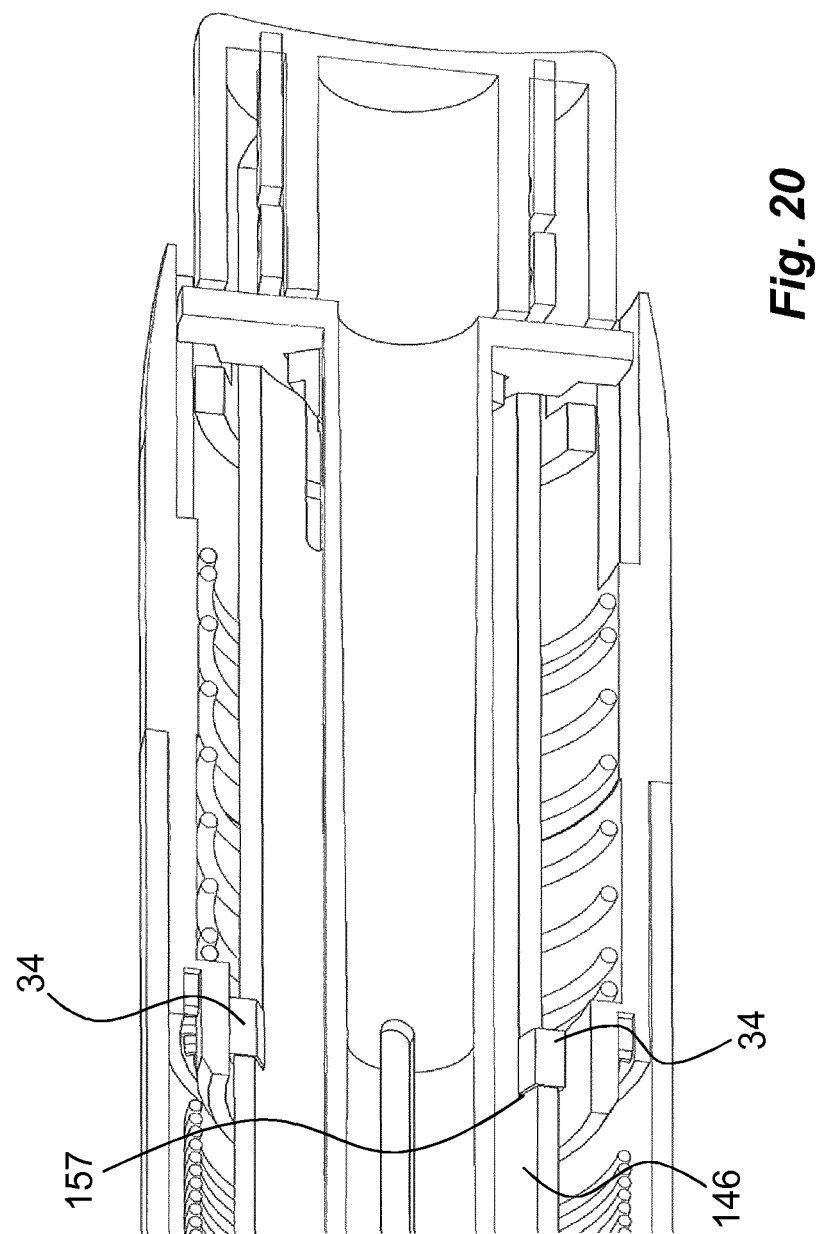
FIG. 20 is a cross-sectional view showing a different functional position.

The movement of the activator 164 in the proximal direction will now cause the annular ledge 150 of the release sleeve 146 to come in contact the distal end connection member 98, whereby the protrusions 152 of the release sleeve 146 will fit into the rectangular cut-outs 108 between the first protrusions 106 of the connection member 98, FIG. 12, wherein the dose setting member 66 will be rotationally locked so that a user cannot manipulate or set a dose at this stage. The dose delivery sequence ends when the guide elements 170 of the plunger rod 172 come in contact with the distally directed end surfaces of the longitudinal grooves 174, FIG. 20.

However, in order to delay the indication that the end of the dose delivery sequence has been reached and in order to ascertain that the medicament container has been completely emptied before removal of the medicament delivery device, the activator 164 and the release sleeve 146 can be moved further in the proximal direction by the resilient section 183 at the distal end of the plunger rod 172, FIG. 21. This further movement will cause the resilient distal part 70 of the dose setting member 66 to compress whereby the connection member 98 will move in the proximal direction. This in turn will cause the second outer protrusions 110 on the distal end of the connection member 98 to move out of contact with the cut-outs 62 of the dose drum 48, FIG. 22, whereby the dose drum 48 is free to rotate and the release of the dose drum 48 will cause it to rotate back to its initial position by the force of the dose drum spring 92.

The stop of the activator 164 and the return of the dose drum 48 will inform the user that it is safe to remove the medicament delivery device 10 from the dose delivery site. The user then releases the activator 164, whereby it is moved distally back to its initial position together with the release sleeve 146 by the activator return spring 192 when the ledges 157 of the release sleeve 146 abuts the guide ledges 34, FIG. 23. The user then replaces the protective cap 44, either with the medicament delivery member 126 on, or with the medicament delivery member 126 removed and discarded.

Thus, each time the user is to administer a dose of medicament the above described steps are performed. When the medicament container is almost empty, it is not possible to set a dose larger than the remaining dose. This is due to the protrusions 128 on the medicament container holder 112, because when the medicament container holder 112 is moved in the distal direction during dose setting, the protrusions 128 will be moved in contact with a proximally directed surface of the dose setting member 66, preventing any further movement of the medicament container holder 112 and thereby the medicament container 114. When the medicament container 114 is empty, the medicament delivery device 10 is discarded in a safe way.

It is to be understood that the embodiment described above and shown in the drawings is to be regarded only as a non-limiting example of the disclosure and that it may be modified in many ways within the scope of the patent claims.

The invention claimed is:

1. A medicament delivery device comprising:
   a housing;
   a medicament container holder, arranged movable in relation to said housing and capable of accommodating a medicament container;
   an activator comprising a plunger rod, which plunger rod is arranged to be moved in a proximal direction of the medicament delivery device by the activator to act on a stopper of the medicament container for delivering a dose of medicament through a medicament delivery member when said activator is operated; and
   a delay mechanism arranged between the activator and the plunger rod, provided with delay elements comprising generally circumferentially extending slits that allow movement of the activator in the proximal direction after movement of the plunger rod has terminated.

2. The medicament delivery device according to claim 1, wherein the generally circumferentially extending slits exert a resilient force between the plunger rod and the activator.

3. The medicament delivery device according to claim 2, wherein the resilient force is chosen larger than the force required to move the stopper when delivering a dose.

4. The medicament delivery device according to claim 3, wherein said delay mechanism comprises a generally tubular body and wherein the generally circumferentially extending slits have areas of material between each successive slit, forming a unit, that several units are placed adjacent each other in a longitudinal direction of the tubular body, wherein areas of material of adjacent units are placed offset in the circumferential direction.

5. The medicament delivery device according to claim 4, wherein the material of the tubular body displays resilient properties.

6. The medicament delivery device according to claim 2, wherein the generally circumferentially extending slits comprise spring elements.

7. The medicament delivery device according to claim 1, further comprising a manually operable dose setting member operably connected to both said housing and said medicament container holder such that manual operation of said dose setting member will cause the medicament container holder with the medicament container to move towards said plunger rod for setting a dose of medicament to be delivered.

8. The medicament delivery device according to claim 7, further comprising a dose drum releasably connected to the dose setting member through a releasable connection mechanism such that when the dose setting member is operated, said dose drum is displaced from an initial position to a set dose position; and
   a release mechanism operably connected to said activator, wherein, when said activator is moved to an end position of the dose delivery operation after movement of the plunger rod has terminated, said release mechanism is arranged to act on said connection mechanism for releasing said dose drum from said dose setting member.

9. The medicament delivery device according to claim 8, further comprising a first resilient member arranged between said dose drum and the housing, which first resilient member is tensioned when the dose setting member is operated such that the dose drum is displaced from the initial position to the set dose position, and wherein said first resilient member is capable of moving said dose drum back from the set dose position to the initial position when said dose drum is released from said dose setting member.

10. The medicament delivery device according to claim 8, wherein the release mechanism comprises a release sleeve.

11. The medicament delivery device according to claim 10, wherein the activator and the release sleeve can be moved further in the proximal direction by the resilient element at the distal end of the plunger rod in order to delay the indication that the end of the dose delivery sequence has been reached and to ascertain that the medicament container has been completely emptied before removal of the medicament delivery device from the injection site.

12. The medicament delivery device according to claim 8, wherein said connection mechanism comprises at least one protrusion operably connected to one of said dose setting member or dose drum engageable with at least one cut-out on the other of said dose drum or dose setting member.

13. The medicament delivery device according to claim 8, further comprising a dose limiting mechanism operably arranged between said dose drum and said housing, capable of limiting the maximum dose to be set, wherein said dose limiting mechanism comprises a groove extending a distance along the circumference of said dose drum arranged to interact with a stop protrusion on said housing, wherein the turning of the dose setting member will bring the stop protrusion in contact with the end of said groove within one turn of the dose setting member, limiting the maximum dose to be set.

14. The medicament delivery device according to claim 7, wherein said dose setting member comprises first locking elements configured to interact with corresponding second locking elements of the medicament container holder for releasably locking rotational positions of said dose setting member during setting of a dose and for providing tactile and audible information during setting of a dose, wherein said first locking elements are protrusions on the inner surface of the dose setting member and the corresponding second locking elements are recess on the outer surface of the medicament container holder.

15. The medicament delivery device according to claim 7, further comprising a last dose mechanism operably arranged between said medicament container holder and said dose setting member and capable of limiting the maximum dose to be set to the remaining quantity of medicament in said medicament container, wherein said last dose mechanism comprises a stop ledge in a proximal area of said medicament container holder, arranged to come in contact with, and limit the movement, of said dose setting member.

16. The medicament delivery device according to claim 15, wherein said activator comprises a return force element arranged to return said activator after delivery of a dose of medicament.

17. A medicament delivery device comprising:
   a housing;
   a medicament container holder slidably attached to the housing and comprising an outer surface having a plurality of locking elements;

an activator comprising a plunger rod that moves in a proximal direction relative to the medicament container holder during dose delivery when said activator is operated; and a delay mechanism axially fixed to the plunger rod and axially moveable relative the activator, the delay mechanism comprises delay elements that allow movement of the activator in a proximal direction after movement of the plunger rod has terminated.

18. The medicament delivery device of claim 17 where the delay elements comprise resilient elements configured as a plurality of circumferentially extending slits that exert a resilient force between the plunger rod and the activator.

19. The medicament delivery device of claim 18 wherein said delay mechanism comprises a generally tubular body and the resilient elements are positioned in tubular body with areas of solid material between each successive slit forming a unit, where several units are placed adjacent each other in a longitudinal direction of the tubular body, wherein areas of material of adjacent units are placed offset in the circumferential direction.

20. The medicament delivery device of claim 17 wherein the locking elements interact with corresponding locking elements located on an inside surface of a dose setting member to releasably lock in rotational positions of the dose setting member during dose setting and for providing tactile and audible information during dose setting.

* * * * *